(12) United States Patent
Shaikh et al.

(10) Patent No.: US 10,975,004 B2
(45) Date of Patent: Apr. 13, 2021

(54) INTEGRATED PROCESS FOR PRODUCTION OF ETHYLENE FROM PROPYLENE

(71) Applicant: Saudi Arabian Oil Company, Dhahran (SA)

(72) Inventors: Sohel Shaikh, Dhahran (SA); Raed Abudawoud, Dhahran (SA); Zhonglin Zhang, Dhahran (SA); Munir Khokhar, Dhahran (SA); Miao Sun, Dhahran (SA)

(73) Assignee: SAUDI ARABIAN OIL COMPANY

( * ) Notice: Subject to any disclaimer, the term of this patent is extended or adjusted under 35 U.S.C. 154(b) by 0 days.

(21) Appl. No.: 16/729,147

(22) Filed: Dec. 27, 2019

(65) Prior Publication Data
US 2020/0216372 A1    Jul. 9, 2020

Related U.S. Application Data

(60) Provisional application No. 62/787,827, filed on Jan. 3, 2019.

(51) Int. Cl.
*C07C 6/04*    (2006.01)
*B01J 37/02*    (2006.01)
(Continued)

(52) U.S. Cl.
CPC ............ *C07C 6/04* (2013.01); *B01J 37/0201* (2013.01); *C07C 2/10* (2013.01); *C07C 41/06* (2013.01);
(Continued)

(58) Field of Classification Search
CPC .. C07C 4/06; C07C 6/04; C07C 11/04; C07C 41/06; C07C 11/06; C07C 11/08; C07C 43/046; C07C 2521/08; C07C 2521/12; C07C 2523/30; C07C 2523/36; C07C 2529/40; C07C 2/10; B01J 21/12;
(Continued)

(56) References Cited

U.S. PATENT DOCUMENTS 3,485,890 A    12/1969    Dixon
5,026,935 A    6/1991    Leyshon et al.
(Continued)

FOREIGN PATENT DOCUMENTS

| CN | 107973684 A | 5/2018 |
| CN | 207347428 U | 5/2018 |
| WO | 2015055594 A1 | 4/2015 |
| WO | 2017003818 A1 | 1/2017 |

OTHER PUBLICATIONS

International Search Report and Written Opinion for related PCT application PCT/US2020/012184 dated Apr. 24, 2020.

*Primary Examiner* — Sharon Pregler
(74) *Attorney, Agent, or Firm* — Bracewell LLP; Constance R. Rhebergen

(57) ABSTRACT

Provided here are methods and systems to enhance the production of ethylene and MTBE from propylene using integrated metathesis and cracking processes. Also disclosed is a method for producing ethylene by at least partially metathesizing propylene in the presence of a metathesis catalyst in a reactor to produce ethylene and butenes, and at least partially cracking the butenes to further produce ethylene using a cracking catalyst positioned downstream of the metathesis catalyst in the same reactor, and further producing MTBE.

20 Claims, 5 Drawing Sheets

(51) Int. Cl.
  *C07C 2/10*    (2006.01)
  *C07C 41/06*   (2006.01)
  *B01J 21/12*    (2006.01)
  *B01J 23/36*    (2006.01)

(52) U.S. Cl.
  CPC ............... *B01J 21/12* (2013.01); *B01J 23/36* (2013.01); *B01J 2219/2419* (2013.01); *C07C 2521/12* (2013.01); *C07C 2523/36* (2013.01)

(58) Field of Classification Search
  CPC .... B01J 2208/00017; B01J 2208/00539; B01J 2208/00628; B01J 2219/2419; B01J 23/36; B01J 37/0201; B01J 8/04
  See application file for complete search history.

(56) References Cited

U.S. PATENT DOCUMENTS

| | | |
|---|---|---|
| 9,079,159 B2 | 7/2015 | Nicholas et al. |
| 9,834,497 B2 | 12/2017 | Shaikh |
| 9,884,794 B2 | 2/2018 | Al-Khattaf et al. |
| 10,059,645 B2 | 8/2018 | Shaikh et al. |
| 10,329,225 B2 | 6/2019 | Khokhar |
| 2006/0047176 A1 | 3/2006 | Gartside et al. |
| 2009/0062589 A1* | 3/2009 | Krupa ........................ C07C 6/04 585/800 |
| 2018/0057425 A1* | 3/2018 | Shaikh .................... B01J 23/30 |
| 2018/0208524 A1 | 7/2018 | Alshafei et al. |
| 2018/0208526 A1 | 7/2018 | Alshafei et al. |

\* cited by examiner

INTEGRATED PROCESS FOR PRODUCTION OF ETHYLENE FROM PROPYLENE

RELATED APPLICATION

This application claims priority from U.S. Provisional Patent Application No. 62/787,827 filed on Jan. 3, 2019, the disclosure of which is incorporated herein by reference in its entirety.

TECHNICAL FIELD

The disclosure relates to the integrated methods and systems for increased production of ethylene from propylene involving catalytic conversions.

BACKGROUND

Ethylene is the one of the most important organic chemicals, by tonnage, that is manufactured in the world. It is usually produced in steam-cracking units from a variety of hydrocarbon feedstocks, and is used in the manufacture of several major derivatives, such as polyethylene, ethylene oxide, ethylene dichloride, polystyrene, and alpha-olefins. In certain regions of the world, such as the United States of America, Canada, and the Middle East, ethane and propane are subject to cracking to produce ethylene and propylene. Purposefully increasing the production of ethylene from propylene streams has been challenging.

SUMMARY

Various embodiments of this disclosure were developed to address these shortcomings in the art. Certain embodiments disclosed and described here include methods of producing ethylene and methyl tertiary-butyl ether (MTBE) from propylene by an integrated metathesis and cracking process in a reactor. One such method for producing ethylene and MTBE includes the steps of supplying a propylene feed stream including at least 80 weight percent propylene to a reactor, where the reactor includes a metathesis reaction zone with a metathesis catalyst positioned upstream of a cracking reaction zone with a cracking catalyst, followed by at least partially metathesizing the propylene in the propylene feed stream with the metathesis catalyst to produce a metathesis reaction product where the metathesis reaction product includes butene and ethylene, and at least partially cracking the metathesis reaction product with the cracking catalyst to produce a cracking reaction product. The method further includes removing from the reactor a reactor product stream including propylene, butene, and ethylene, and fractionating the reactor product stream in an ethylene fractionation unit to produce an ethylene product and a C3+ stream including butene and propylene, followed by supplying the C3+ stream to a propylene fractionation unit. The method further includes fractionating the C3+ stream to produce a propylene recycle and a C4+ stream including butene, and supplying the C4+ stream to a butene fractionation unit. The method further includes fractionating the C4+ stream in the butene fractionation unit to produce a butene stream and a C5+ stream. The method further includes supplying the propylene recycle to the reactor and supplying the butene stream to an MTBE unit.

In some embodiments, the method can further include the steps of supplying a methanol stream to the MTBE unit, producing a butene residual in the MTBE unit, where the butene residual includes 1-butene and 2-butene, and producing an MTBE product in the MTBE unit, where the MTBE product includes MTBE. In some embodiments, the method further includes the step of removing impurities from a feed stream in an impurities removal unit to produce a clean propylene feed stream. The method can include the step of heating the clean propylene feed stream in a heat exchanger to produce a hot propylene feed stream. The method can also include the step of heating the propylene feed stream using a heater to produce the propylene feed steam. The method can also include the step of cooling the reactor product stream in the heat exchanger, where the heat exchanger is a cross-exchanger.

In certain embodiments of this method, the propylene conversion rate is greater than 40 percent. In some embodiments, the butene residual also includes isobutylene, where the isobutylene is be less than about 10 weight percent of the butene residual.

In some embodiments of this method, the metathesis catalyst includes a mesoporous silica catalyst impregnated with metal oxide, where the mesoporous silica catalyst includes a pore size distribution of 2.5 nm to 40 nm and a total pore volume of at least 0.6 $cm^3/g$, and the cracking catalyst includes a mordenite framework inverted (MFI) structured silica catalyst with a total acidity ranging from 0.001 mmol/g to 0.1 mmol/g.

In certain embodiments, the method also includes the step of recycling the butene residual to the reactor. In some embodiments, the reactor is operated between about 500° C. and 600° C., and between about atmospheric pressure and 2 atmospheres of pressure.

Certain embodiments disclosed and described here include a system of producing ethylene and methyl tertiary-butyl ether (MTBE) from propylene in an integrated metathesis and cracking process in a reactor. One such system for producing ethylene and MTBE includes a reactor where the reactor is configured to convert a propylene feed stream to a reactor product stream, where the reactor has a metathesis reaction zone positioned upstream of a cracking reaction zone, where the metathesis reaction zone has a metathesis catalyst including a mesoporous silica catalyst impregnated with metal oxide; and where the cracking reaction zone has a cracking catalyst including a mordenite framework inverted (MFI) structured silica catalyst; and where the reactor is configured to operate between about 500° C. and 600° C., and between about atmospheric pressure and 2 atmospheres of pressure. The reactor produces a reactor product stream including propylene, ethylene, and butene. The system further includes an ethylene fractionation unit fluidically connected to the reactor, where the ethylene fractionation unit is configured to operate at a pressure, temperature, and condition to separate an ethylene product from the reactor product stream. The system also includes a propylene fractionation unit fluidically connected to the ethylene fractionation unit, where the propylene fractionation unit is configured to operate at a pressure, temperature, and condition to separate a propylene recycle from the reactor product stream. The system also includes a butene fractionation unit fluidically connected to the propylene fractionation unit, where the butene fractionation unit is configured to operate at a pressure, temperature, and condition to separate butene from the reactor product stream, and an MTBE unit fluidically connected to the butene fractionation unit, where the MTBE unit is configured so that it produces a butene residual and an MTBE product.

In certain embodiments, the system includes a metal oxide of the mesoporous silica catalyst that includes one or more oxides of molybdenum, rhenium, tungsten, or combinations thereof. In some embodiments, the system uses a MFI structured silica catalyst that is alumina free. In some embodiments, the system uses a MFI structured silica catalyst that includes alumina. In certain embodiments, the MTBE unit is fluidically connected to the reactor and the butene residual is supplied to the reactor. In some embodiments, the system includes an impurities removal unit fluidically connected upstream of the reactor. In some embodiments, a heater is provided to heat the propylene feed stream before the propylene feed stream is introduced to the reactor. In some embodiments, a heat exchanger is provided to heat the propylene feed stream before entering the reactor and cool the reactor product stream after leaving the reactor. In some embodiments, the system includes the reactor which is configured to react the propylene feed stream including greater than 80 weight percent of propylene to produce the reactor product stream including greater than 40 weight percent of ethylene.

Numerous other aspects, features and benefits of the present disclosure can be made apparent from the following detailed description taken together with the drawings. The methods can include other additional fractionation steps or different reactor components depending on desired goals.

BRIEF DESCRIPTION OF THE DRAWINGS

Embodiments will be readily understood by the following detailed description in conjunction with the accompanying drawings. Embodiments are illustrated by way of example and not by way of limitation in the accompanying drawings.

Figure 1:
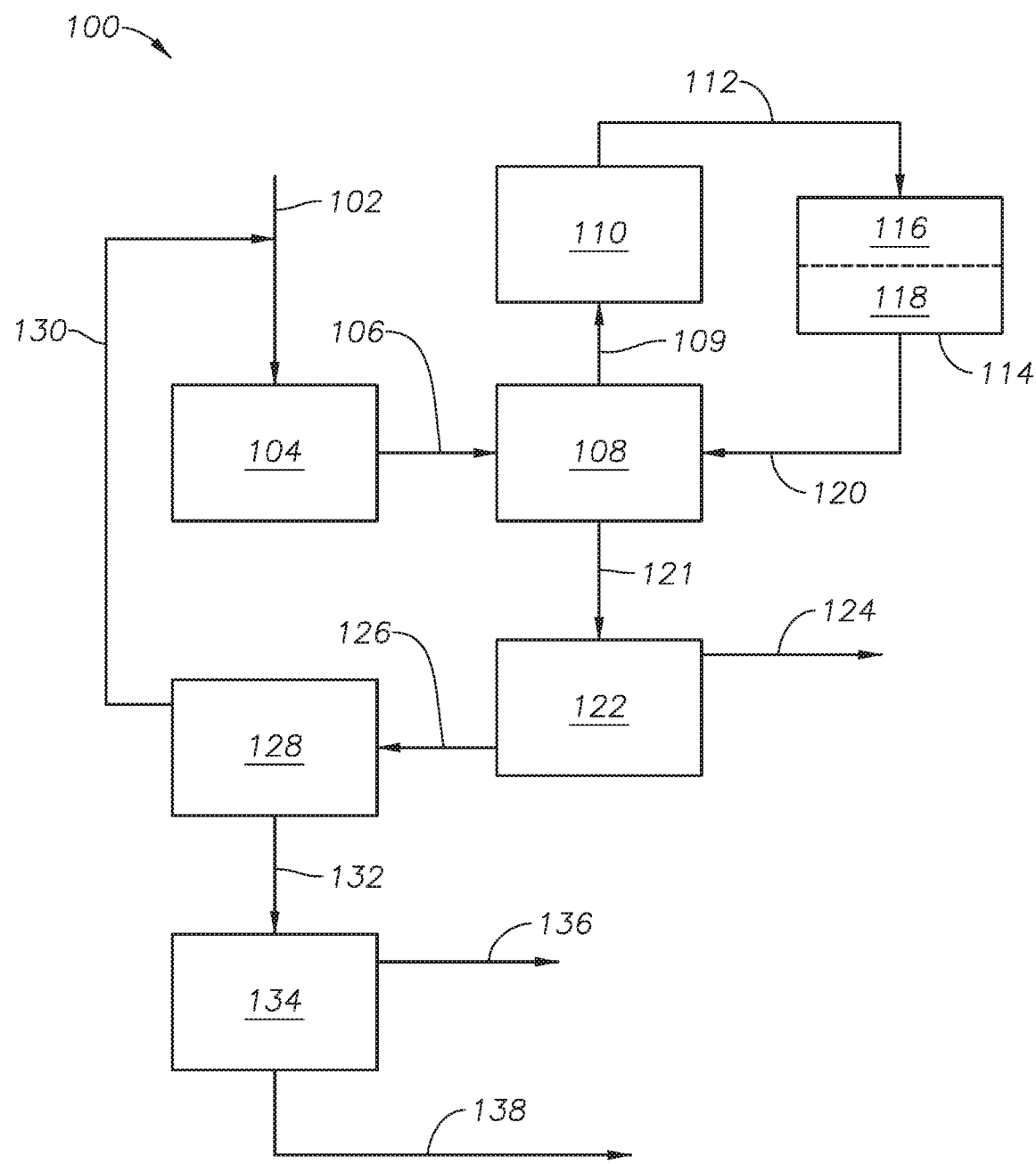
FIG. 1 is a block diagram of an ethylene production system with a dual-zone catalyst configuration in a reactor, according to an embodiment.

In the accompanying Figures, similar components or features, or both, may have a similar reference label. For the purpose of the simplified schematic illustrations and descriptions of FIGS. 1 and 2, the numerous pumps, valves, temperature and pressure sensors, electronic controllers, and the like that can be employed and well known to those of ordinary skill in the art of certain refinery operations are not included. Transfer lines between the various components of the system can include pipes, conduits, channels, or other suitable physical transfer lines that connect by fluidic communication one or more system components to one or more other system components. Further, accompanying components that are in conventional refinery and industrial operations including catalytic conversion processes such as air supplies, catalyst hoppers, and flue gas handling are not depicted. However, operational components, such as those described in the present disclosure, can be added to the embodiments described in this disclosure.

It should further be noted that arrows in the drawings refer to transfer lines which can serve to depict streams between two or more system components. Additionally, arrows that connect to system components define inlets or outlets in each given system component. The arrow direction corresponds generally with the major direction of movement of the materials of the stream contained within the physical transfer line signified by the arrow. Furthermore, arrows which do not connect two or more system components signify a product stream which exits the depicted system or a system inlet stream which enters the depicted system. Product streams can be further processed in accompanying chemical processing systems or can be commercialized as end products. System inlet streams can be streams transferred from accompanying chemical processing systems or can be processed or non-processed feedstock streams.

DETAILED DESCRIPTION

The present disclosure describes various embodiments related to methods and system of converting propylene into ethylene and butene, and further producing MTBE. In the following description, numerous details are set forth in order to provide a thorough understanding of the various embodiments. In other instances, well-known processes, devices, and systems may not been described in particular detail in order to refrain from unnecessarily obscuring the various embodiments. Additionally, illustrations of the various embodiments may omit certain features or details in order to not obscure the various embodiments. The systems described in this disclosure also include apparatuses known in the art as required in hydrocarbon treatment plants, such as, but not limited to, separation units, reactors, heat transfer devices such as heaters and heat exchangers, filters, impurities removal devices, analyzers, such as in-line chromatography devices, combinations of each, and the like. A transfer line, such as pipes, conduits, channels, or other suitable connectors can generally carry a process stream between two or more system components. Generally, the chemical composition of a process stream in a particular transfer line is similar or identical throughout the entire length of the transfer line. However, it should be appreciated that the temperature, pressure, or other physical properties of a process stream can change through a transfer line, particularly in different transfer line segments. Also, relatively minor compositional changes in a process stream can take place over the length of a transfer line, such as the settling of an impurity or formation of condensates.

In the following detailed description, reference is made to the accompanying drawings that form a part of this disclosure. The drawings can provide an illustration of some of the various embodiments in which the subject matter of the present disclosure can be practiced. Other embodiments can be utilized, and logical changes can be made without departing from the scope of this disclosure.

Disclosed herein are methods and systems for producing ethylene and butenes from propylene. The butenes can further be used to generate MTBE. In an embodiment, the method includes introducing propylene to a reactor, performing the metathesis of propylene to produce a metathesis reaction product containing butenes and ethylene, followed by the cracking of the propylene and butenes to produce a cracking reaction product containing ethylene and other olefins. In some embodiments, the metathesis catalyst contains a mesoporous silica catalyst impregnated with a metal oxide, and the cracking catalyst contains an MFI structured silica catalyst. Without being bound by any theory, it is believed that the propylene is converted to ethylene and butenes by self-metathesis. The butenes and other olefins can then be catalytically cracked with a cracking catalyst to produce additional ethylene and other olefins. The order of metathesis then cracking advantageously improves ethylene yield. The method further includes removing from the reactor a reactor product stream containing reaction products and unreacted propylene. The method further includes fractionating the reactor product stream to produce ethylene and a C3+ stream. In certain embodiments, the method includes fractionating the C3+ stream to produce propylene and a C4+ stream. The propylene can be recycled to the reactor. In certain embodiments, the propylene can be recycled to the reactor and can undergo self-metathesis to extinction. In certain embodiments, the method further includes fractionating the C4+ stream to produce butenes and a C5+ stream. In certain embodiments, the butenes are sent to an MTBE unit. In some embodiments, both butenes and methanol are supplied to the MTBE unit to produce a MTBE product and a butene residual. In some embodiments, the butene residual is recycled to the reactor to generate additional cracking products.

The methods and systems disclosed herein provide many advantages. The methods and systems of this disclosure use propylene as a feedstock, which is advantageous if there is no downstream market that can accept propylene from a facility, or if there is no other way to convert the propylene to another saleable product such as polypropylene. Additionally, the methods and systems can accept a variety of grades of propylene as a feedstock, promoting flexibility and economic benefit to the operator. The propylene self-metathesis which occurs in the metathesis portion of the reactor produces ethylene and butenes, specifically the isomer 2-butene. The production of 2-butene is advantageous because the isomer can undergo additional reactions, including second order, third order, and fourth order reactions, such as cracking, metathesis, and oligomerization to produce additional ethylene. The propylene self-metathesis is limited by equilibrium, but the cracking reaction section allows for additional ethylene production above and beyond what the propylene self-metathesis can provide. Advantageously, the system uses one reactor that contains two sets of catalysts instead of two reactors, reducing complexity and the need for a high capital expense of additional separation units. Unreacted or subsequently generated propylene can be recycled directly to the same reactor instead of a separate reactor. Embodiments include processes and systems of adapting existing units to manufacture ethylene and MTBE from propylene, 1-hexene, 1-octene and alpha olefins, and combinations of the same, by selection of appropriate catalysts in the dual catalyst configuration. With the novel combination of metathesis and cracking catalysts disclosed here, the ethylene yield is improved by 10-30%. Additionally, the ethylene selectivity with the combination of the propylene feed and the metathesis and cracking catalysts is approximately 30% to 50%, a significant enhancement as compared to other comparable processes. The processes in this disclosure advantageously use propylene based feedstocks to generate both ethylene and butene. Disclosed embodiments include processes and systems of adapting existing units to maximize ethylene production from propylene when the ethylene demand and prices exceed those of propylene. The disclosed methods and systems provide flexibility to change the mode of operation between production of ethylene and propylene in response to changes in market conditions simply by changing the feed streams and quality.

The butenes generated by the methods and systems can be further processed, cracked to form additional ethylene, or used to produce MTBE. By routing the butene stream generated from the reaction process to an MTBE unit, the isobutylene can be consumed leaving a butene residual. The disclosed MTBE unit is advantageous because it promotes the use of the butene stream, which can contain isobutylene, 1-butene, and 2-butene, and combinations of the same. The MTBE unit acts similarly to a reactive separation by consuming the isobutylene and leaving the residual 1-butene and 2-butene, which in some embodiments can be recycled back to the reactor to create additional ethylene. This allows for a butene residual recycle to the reactor allowing the butenes to undergo the cracking reaction to produce additional ethylene product. Therefore, the process can generate an additional product stream (MTBE) while simultaneously removing an unfavored butene isomer (isobutylene) from a recycle stream to generate a more optimized butene stream, which can be recycled to generate an additional ethylene product. Additionally, the disclosed methods and systems advantageously produces a butene stream that is 40-50 wt % isobutylene, which is a suitable feed for the MTBE unit.

The description may use the phrases "in some embodiments," "in an embodiment," or "in embodiments," which can each refer to one or more of the same or different embodiments. Furthermore, the terms "comprising," "including," "containing," and the like, as used with respect to embodiments of the present disclosure, are synonymous.

For the purposes of describing and defining the present disclosure, a composition that "substantially contains" a particular compound includes at least 51% by weight of that particular compound (for example, ethylene, propylene, or butenes). As used herein, a composition that is "substantially free" of a particular compound includes no more than 1% by weight of that particular compound. As used in this disclosure, the term "about" is utilized to represent the inherent degree of uncertainty that may be attributed to any quantitative comparison, value, measurement, or other representation. The term "about" is also utilized in this disclosure to represent the degree by which a quantitative representation can vary from a stated reference without resulting in a change in the basic function of the subject matter at issue.

As used in this disclosure, a "fractionator" refers to any separation device that at least partially separates one or more chemicals that are mixed in a process stream from one another. For example, a fractionator can selectively separate differing chemical species from one another, producing one or more chemical fractions. Examples of fractionators include, without limitation, distillation columns, flash drums, membrane separators, solvent extraction systems, and the like. It should be understood that separation processes described in this disclosure may not completely separate all of one chemical component from all of other chemical components. It should be understood that the separation processes described in this disclosure, including fractionators, at least partially separate one chemical component from another component or from other components in a stream. Even if not explicitly stated, it should be understood that separation can include only partial separation. As used in this disclosure, one or more chemical constituents can be "separated" from a process stream to form a new process stream. Generally, a process stream can enter a fractionator and be divided, or separated, into two or more process streams of desired composition. In another embodiment, separation and reactions can take place in a reactive separation unit.

As used in this disclosure, a "reactor" refers to a vessel in which one or more chemical reactions can occur between one or more reactants optionally in the presence of one or more catalysts. For example, a reactor can include a tank or tubular reactor configured to operate as a batch reactor, a continuous stirred-tank reactor, or a plug flow reactor. Examples of reactors include packed bed reactors, such as fixed bed reactors and fluidized bed reactors. As used in this disclosure, a "zone" is a whole or a part of a working volume of a reactor. In an embodiment, a zone can contain a particular catalyst or a mixture of multiple catalysts to carry out one or more specific reactions. In certain embodiments, a reactor can have multiple zones, such that multiple catalysts are presented within a single reactor, but in separate and defined zones. In these embodiments, the catalysts function discretely and are not intermingled.

As used in this disclosure, a "unit" refers to a system of one or more vessels in which one or more physical or chemical processes can occur. For example, a unit can include the system of a reactor, a distillation column, pumps, compressors, and a heater, as well as other necessary equipment known in the art. The unit can function as a process to generate a desired product or complete a desired process.

As used in this disclosure, a "catalyst" refers to any substance which increases the rate of a specific chemical reaction or increases the selective production of certain products in a reaction. Catalysts described in this disclosure can be utilized to promote various reactions, such as, but not limited to, metathesis or cracking reactions, or both. Catalysts described in this disclosure can also aid in isomerization, or can increase the selective production of certain isomers in a reaction. As used in this disclosure, a "metathesis catalyst" increases the rate of a metathesis reaction or increases the production of selective products of a metathesis reaction. As used in this disclosure "metathesis" generally refers to a chemical reaction where fragments of alkenes are redistributed by the scission and regeneration of alkene bonds. For example, a propylene self-metathesis reaction involves two propylene molecules reacting in the presence of a suitable catalyst to make ethylene and 2-butene. Other compounds can be produced as a result of side reactions; such other compounds can include 1-butene, pentenes, hexenes, and combinations of the same. A "cracking catalyst" increases the rate of a cracking reaction. As used in this disclosure, "cracking" generally refers to a chemical reaction where a larger molecule having one or more carbon to carbon bonds is broken into more than one smaller molecule by the breaking of one or more of the carbon to carbon bonds. For example, cracking of butene can produce propylene and ethane; alternatively, it can produce ethylene and other olefins. Cracking reaction products can include ethylene, propylene, butene, pentenes, and hexenes from β-scission; ethane, propane, butane, pentane, and hexane from hydride transfer reactions; aromatics and cokes from alkylation, cyclization, and hydride transfer reactions. Secondary cracking reactions can also occur, resulting in additional $C_2$ and $c_3$ species.

Embodiments of the methods and systems disclosed here include configurations that maximize the production of ethylene, butene, and MTBE. In an embodiment, a two-zoned catalyst configuration is used to maximize ethylene and butene yield. FIG. 1 is a block diagram of an ethylene and butene production system 100 with a dual-zone catalyst configuration in a reactor, according to one or more embodiments described in this disclosure. A feed stream 102 containing propylene is optionally supplied to an impurities removal unit 104. The feed stream 102 can include at least about 65 wt % alternately about 70 wt %, alternately about 75 wt %, alternately about 80 wt %, alternately about 90 wt %, alternately about 95 wt %, and alternately at least about 99 wt % propylene. The feed stream can further include $C_2$ components, other $C_3$ components, $C_4$-$C_5$ components, $C_{6+}$ components, and combinations of the same. In at least one embodiment, the feed stream 102 includes about 10 wt %, alternately about 8 wt %, alternately about 4 wt %, alternately about 2 wt %, alternately about 1 wt %, and alternately less than about 1 wt % ethylene. In at least one embodiment, the feed stream 102 further contains less than 1 wt % of $C_2$ components, other $C_3$ components, $C_4$-$C_5$ components, and combinations of the same. In another embodiment, the feed stream 102 further contains less than 5 wt % of $C_2$ components, other $C_3$ components, $C_4$-$C_5$ components, and combinations of the same. In at least one embodiment, the feed stream 102 can contain less than 5 wt % of $C_{6+}$ components and alternately less than 1 wt % of $C_{6+}$ components. Other $C_3$ components can include propane. In an embodiment, the feed stream 102 can contain less than 30 wt % propane, and alternately less than 20 wt % propane. In at least one embodiment, the feed stream 102 is in the absence of butene. In at least one embodiment, the feed stream 102 is a refinery grade propylene with between about 65 wt % and about 75 wt % propylene. In another embodiment, the feed stream 102 is a chemical grade propylene with between about 92 wt % and 96 wt % propylene. In yet another embodiment the feed stream 102 is a polymer grade propylene, with about 99.5 wt % propylene. The impurities removal unit 104 can include any unit known in the art that can remove impurities. Impurities can include oxygenates such as alcohols, particularly methanol, ethanol, and higher alcohols or their derivatives. The impurities removal unit 104 can include a catalytic bed or adsorbers.

A clean feed stream 106 containing propylene can exit the impurities removal unit 104 and can be preheated by heating elements, such as a heat exchanger 108 and a heater 110. Heat exchanger 108 can be a cross-exchanger capable of removing heat from one process stream and supplying the removed heat to another process stream, such that no heat transfer fluid is used. Heat exchanger 108 can produce hot propylene feed stream 109. Examples of inlet and outlet temperatures of the cold side component of the heat exchanger 108 are about 50-100 degrees Celsius (° C.) and about 200-300° C., respectively. Examples of inlet and outlet temperatures of the hot side component of the heat exchanger 108 are about 550-600° C. and about 300-400° C., respectively. Hot propylene feed stream 109 can be introduced to heater 110. Heater 110 can be a fired heater. Heater 110 can generate a propylene feed stream 112 at a temperature optimized for undergoing metathesis and cracking reactions with the catalysts. Examples of inlet and outlet temperatures of the heater 110 are about 200-300° C. and about 550-600° C., respectively. It is not required for the propylene feed stream 112 to come from the heater 110 or from the heat exchanger 108.

The heat exchanger 108 and the heater 110 can serve to elevate the temperature of the feed stream 102 or the clean propylene feed stream 106, either by exchanging energy with other streams in the system, such as stream 120, or by direct heating. The impurities removal unit 104, the heat exchanger 108, and the heater 110 are optional components in the ethylene and butene production system 100.

After optional impurities removal and heating, the propylene feed stream 112 can be transferred to a reactor 114.

The propylene feed stream 112 can have the same composition as feed stream 102, optionally in the absence of impurities.

The propylene feed stream 112 is fed into a reactor 114 containing two zones, a metathesis reaction zone 116 and a cracking reaction zone 118. The metathesis reaction zone 116 contains a metathesis catalyst and the cracking reaction zone 118 contains a cracking catalyst. The metathesis reaction zone 116 is positioned generally upstream of the cracking reaction zone 118. In an alternate embodiment, the metathesis reaction zone 116 can be positioned downstream of the cracking reaction zone 118. In an alternate embodiment, the two zones can overlap or intertwine. The two catalysts can be separated from each other in the two zones. In an alternate embodiment, the two catalysts can be in contact when the two zones overlap or intertwine. In at least one embodiment, each of the metathesis catalyst and the cracking catalyst can be positioned in discrete catalyst beds inside one reactor as shown in the FIG. 1 and FIG. 2.

The metathesis catalyst in the metathesis reaction zone 116 can convert propylene to ethylene and butenes in metathesis reactions. Examples of catalysts suitable for use as the metathesis catalyst can include metal catalysts supported on oxide supports, or can include mesoporous silica catalysts impregnated with metal oxide. The metal catalysts can include vanadium oxide ($V_2O_5$), tungsten oxide ($WO_3$), or combinations thereof, and the oxide support can be silicon dioxide ($SiO_2$), aluminum oxides ($Al_2O_3$), or other oxides. The metal oxide can include one or oxides of a metal from the Groups 6-10 of the IUPAC Periodic Table. In certain embodiments, the metathesis catalyst is a mesoporous silica catalyst impregnated with metal oxide. In certain embodiments, the metal oxide of the mesoporous silica catalyst includes one or more oxides of molybdenum, rhenium, tungsten, or combinations thereof. The metal oxide of the mesoporous silica catalyst can include tungsten oxide. Any conventional or commercially available metathesis catalyst could be used in this process at an appropriate temperature and pressure, such as supported metal oxides ($ReO_x/Al_2O_3$, $ReO_x/(SiO_2—Al_2O_3)$, $MoO_x/SiO_2$, $MoO_x/Al_2O_3$, $MoO_x/(SiO_2—Al_2O_3)$, $WO_x/SiO_2$, and $WO_x/(SiO_2—Al_2O_3)$), and supported organometallic complexes. The mesoporous silica catalysts can include a pore size distribution of from about 2.5 nm to about 40 nm and a total pore volume of at least about 0.6 cm$^3$/g (cubic centimeters per gram). The pore size distribution denotes the relative abundance of pores of a particular diameter in a representative sample of the catalyst. In one or more embodiments, the metathesis catalyst includes amorphous mesoporous silica foam impregnated with metal oxides. In one or more embodiments, the pore size distribution of the mesoporous silica catalyst can range from about 2.5 nm to about 40 nm, or about 2.5 nm to about 20 nm, or about 2.5 nm to about 4.5 nm, or about 2.5 nm to about 3.5 nm, or about 8 nm to about 18 nm, or about 12 nm to about 18 nm. In further embodiments, the total pore volume can be from about 0.6 cm$^3$/g to about 2.5 cm$^3$/g, or about 0.6 cm$^3$/g to about 1.5 cm$^3$/g, or about 0.6 cm$^3$/g to about 1.3 cm$^3$/g, or about 0.6 cm$^3$/g to about 0.8 cm$^3$/g, or about 0.6 cm$^3$/g to about 0.7 cm$^3$/g, or about 0.9 cm$^3$/g to about 1.3 cm$^3$/g.

The cracking catalyst in the cracking reaction zone can crack butene to produce propylene and ethylene. Examples of catalysts suitable for use as the cracking catalyst can include an MFI structures aluminosilicate zeolite catalysts. Examples include a high silica ZSM-5 catalyst. Zeolite Socony Mobil-5 (ZSM-5) is an aluminosilicate zeolite belonging to the pentasil family of zeolites. Any conventional or commercially available cracking catalyst could be used in this process at an appropriate temperature and pressure, such as zeolite-based catalyst compositions containing an active aluminosilicate component. In certain embodiments, the cracking catalysts contain an MFI structure silica catalyst. In certain embodiments, the MFI structured silica catalyst is alumina free. In certain embodiments, the MFI structured silica catalyst contains alumina. For the MFI structured aluminosilicate zeolite catalysts, various amounts of alumina are contemplated. In one or more embodiments, the MFI structured aluminosilicate zeolite catalysts can have a molar ratio of silica to alumina of about 5 to about 5000, or about 100 to about 4000, or about 200 to about 3000, or about 1500 to about 2500, or about 1000 to about 2000. Various suitable commercial embodiments of the MFI structured aluminosilicate zeolite catalysts are contemplated, for example, ZSM-5 zeolites such as MFI-280 produced by Zeolyst International or MFI-2000 produced by Saudi Aramco. In another embodiment, a cracking catalyst which contains a MFI structured silica catalyst is utilized. The MFI structured silica catalyst can include a pore size distribution of from about 1.5 nm to 3 nm, or about 1.5 nm to 2.5 nm. Furthermore, the MFI structured silica catalyst can have a surface area of from about 300 m$^2$/g to about 425 m$^2$/g, or about 340 m$^2$/g to about 410 m$^2$/g. Additionally, the MFI structured silica catalyst can have a total acidity of from about 0.001 mmol/g to about 0.1 mmol/g, or about 0.01 mmol/g to about 0.08 mmol/g. The acidity can be maintained at or less than about 0.1 mmol/g in order to reduce production of undesirable byproducts such as aromatics. Increasing acidity can increase the amount of cracking; however, this increased cracking can also lead to less selectivity and increased production of aromatic byproducts, which can lead to catalyst coking and deactivation. Without being bound by any theory, it is believed that the increasing cracking catalyst acidity can cause alkenes to undergo oligomerization reactions forming C5+ alkenes, which can undergo hydride transfer, cyclization, alkylation, de-alkylation, and dehydrogenation reactions leading to aromatic and coke formation.

The suitable reaction conditions in the reactor 114 for metathesis reactions and cracking reactions described in this disclosure can vary by the catalyst compositions employed. In an embodiment, the operating conditions of the reactor 114 include operating temperatures ranging from 400-600° C. and pressures ranging from 1 standard atmospheric pressure (atm) to 2 atm. The operating temperatures of the reactor 114 can range from about 400-600° C., alternately about 400-500° C., alternately about 500-550° C., alternately about 500-600° C., and alternately about 550-600° C. In an embodiment, the preferred temperature ranges for optimal performance may be different for both catalyst beds; therefore, the metathesis reaction zone 116 operates at a temperature between about 400° C. and about 500° C., and the cracking reaction zone 118 operates at a temperature between about 500° C. and 600° C. A higher operating temperature can provide higher ethylene yields; however, the higher operating temperature can result in side-product formation. At a lower operating temperature in the reactor 114, the recycle stream to the reactor 114 can be larger. The reactor 114 operating temperature during start of operations can be at a lower temperature, such as about 280° C. The operating pressure of the reactor 114 can be in the range from atmospheric pressure to 30 atm, alternately at about atmospheric pressure, alternately about 1 atm, alternately in the range from about 1-2 atm, and alternately in the range from about 1-5 atm. The hourly volumetric feed gas flow rate per reaction volume in the reactor 114 can be about 10-30 per hour (expressed as h$^{-1}$) or about 1-10 hr$^{-1}$. The weight hourly space velocity (WHSV) expressed as the mass flowrate of reactants divide by the mass of catalysts in the reactor vessel can be 2-10. In an embodiment, the WHSV is 3-5. Various amounts of each catalyst can be present in this dual catalyst system. The ratio by volume of metathesis catalyst to cracking catalyst can range from about 5:1 to about 1:5, alternately from about 2:1 to about 1:2, and alternately from about 1:1.

Returning to FIG. 1 and FIG. 2, the propylene feed stream 112 contacts the metathesis catalyst to undergo a metathesis reaction in the metathesis reaction zone 116 to produce a metathesis reaction product. In at least one embodiment, the propylene in propylene feed stream 112 is metathesized. In at least one embodiment, propylene feed stream 112 is partially metathesized. The metathesis reaction product can include ethylene, propylene, butene, and combinations of the same. The propylene can include unreacted propylene from propylene feed stream 112. Following the metathesis reaction, the metathesis reaction product is contacted with the cracking catalyst to undergo a catalytic cracking reaction in the cracking reaction zone 118 to produce a cracking reaction product. The cracking reaction product can include contains ethylene, butenes, propylene, other olefins, and combinations of the same. In an embodiment of the dual catalyst system, the overall propylene conversion rate can be between 40% and 60% for a single pass. The single pass cracking yield of the butenes in the metathesis reaction product can be about 10 wt % ethylene, and 20-30 wt % propylene.

A reactor product stream 120 exits the reactor 114. The reactor product stream 120 can include the metathesis reaction product, the cracking reaction product, unreacted propylene feed, and combinations of the same. More specifically, the reactor product stream 120 can include ethylene, propylene, butenes, and other hydrocarbons, and combinations of the same. The other hydrocarbons in reactor product stream 120 can include methane, propane, n-butane, isobutane, benzene, toluene, ethylbenzene, xylene, and other $C_5/C_{5+}$ hydrocarbons. The reactor product stream 120 containing ethylene can contain at least about 10 wt %, alternately at least about 15 wt %, alternately at least about 20 wt %, and alternately at least about 25 wt % of ethylene. In certain embodiments, the ethylene in the reactor product stream 120 can range from 30 wt % to 40 wt %. The reactor product stream 120 can contain at least about 10 wt %, alternately at least about 20 wt %, alternately at least about 30 wt %, and alternately at least about 40 wt % butene. In at least one embodiment, the reactor product stream 120 exiting the reactor 114 is passed to the heat exchanger 108 and the temperature of the reactor product stream 120 is reduced to between about 300-400° C. The cooled reactor product stream 121 exiting the heat exchanger 108 can be supplied to the ethylene fractionation unit 122. In at least one embodiment, the reactor product stream 120 is supplied directly to the ethylene fractionation unit 122. The ethylene fractionation unit 122 can be any type of fractionator capable of separating the reactor product stream 120 or cooled reactor product stream 121. Examples of fractionators suitable for use as the ethylene fractionation unit 122 can include a de-ethanizer, a distillation column, and combinations of the same. The ethylene fractionation unit 122 can be operated at a temperature and pressure to recover ethylene and lighter components from the cooled reactor product stream 121 or the reactor product stream 120. The ethylene fractionation unit 122 can be operated at about 15-25 bar. In an embodiment, the ethylene fractionation unit 122 is operated at about 25 bar. The condenser for the ethylene fractionation unit 122 can be operated at about −25° C. to about −15° C. The reactor product stream 120, or the cooled reactor product stream 121, can be fractionated in the ethylene fractionation unit 122 to produce an overhead product and a bottom product. The overhead product from the ethylene fractionation unit 122 is removed as the ethylene product 124. The ethylene product 124 contains ethylene, and can contain at least about 50 wt %, alternately at least about 60 wt %, alternately at least about 70 wt %, alternately at least about 80 wt %, alternately at least about 90 wt %, alternately at least about 92 wt %, alternately at least about 95 wt %, and alternately at least about 99 wt % ethylene.

The bottom product from the ethylene fractionation unit 122 is removed as a C3+ stream 126. The C3+ stream 126 contains $C_3$ or higher hydrocarbons. The $C_3$ or higher hydrocarbons can include propylene, butenes, and combinations of the same. In at least one embodiment, the C3+ stream contains propylene and butenes. The C3+ stream 126 is supplied to the propylene fractionation unit 128. The propylene fractionation unit 128 can be any type of fractionator capable of separating the C3+ stream 126. Examples of fractionators suitable for use as the propylene fractionation unit 128 can include a de-propanizer, a distillation column, and combinations of the same. The propylene fractionation unit 128 can be operated at a temperature and pressure to separate propylene from the C3+ stream 126. The propylene fractionation unit 128 can be operated at about 15-25 bar. In an embodiment, the propylene fractionation unit 128 is operated at about 25 bar. The condenser for the propylene fractionation unit 128 can be operated at about −20° C. to about −10° C. The propylene fractionation unit 128 separates propylene from the $C_4/C_{4+}$ fractions in the C3+ stream 126 to produce a propylene recycle 130 and a C4+ stream 132. The propylene recycle 130 contains propylene. The propylene recycle 130 can contain at least about 50 wt %, alternately at least about 60 wt %, alternately at least about 70 wt %, alternately at least about 80 wt %, alternately at least about 90 wt %, alternately at least about 92 wt %, alternately at least about 95 wt %, alternately at least about 97 wt %, and alternately at least about 99 wt % propylene. In certain embodiments, the propylene recycle 130 is recycled to the feed stream 102, or, in another embodiment, is provided along with the propylene feed stream 112 to the reactor 114. The propylene recycle 130 can alternatively be removed from the ethylene and butene production system 100, or can be combined with a stream or other process stream upstream of the reactor 114.

In an embodiment, the C4+ stream 132 exiting the propylene fractionation unit 128 contains butenes, and alternately $C_4$ or higher hydrocarbons. The C4+ stream 132 is supplied to a butene fractionation unit 134. The butene fractionation unit 134 can be any type of fractionator capable of separating the C4+ stream 132. Examples of fractionators suitable for use as the butene fractionation unit 134 can include a fractional distillation column, a de-butanizer, and combinations of the same. The butene fractionation unit 134 can separate the C4+ stream 132 to generate a butene stream 136 and a C5+ stream 138. The butene fractionation unit 134 can be operated at a temperature and pressure to separate butenes from the C4+ stream 132. The butene fractionation unit 134 can be operated at about 5-15 bar. In an embodiment, the butene fractionation unit 134 is operated at about 10 bar. The condenser for the butene fractionation unit 134 can be operated at about 60° C.

to about 80° C. The bottom product from the butene fractionation unit 134 is a C5+ stream 138 and substantially contains $C_5$ and $C_{5+}$ hydrocarbons. The butene stream 136 can contain at least about 50 wt %, alternately at least about 60 wt %, alternately at least about 70 wt %, alternately at least about 80 wt %, alternately at least about 90 wt %, alternately at least about 92 wt %, alternately at least about 95 wt %, and alternately at least about 99 wt % butenes. The butene stream 136 can contain isomers of butenes such as 1-butene, 2-butene, and isobutylene, and combinations of the same. The butene stream 136 can advantageously contain a range of isobutylene of 40-50 wt %, which is a suitable feed for an MTBE unit.

Figure 2:
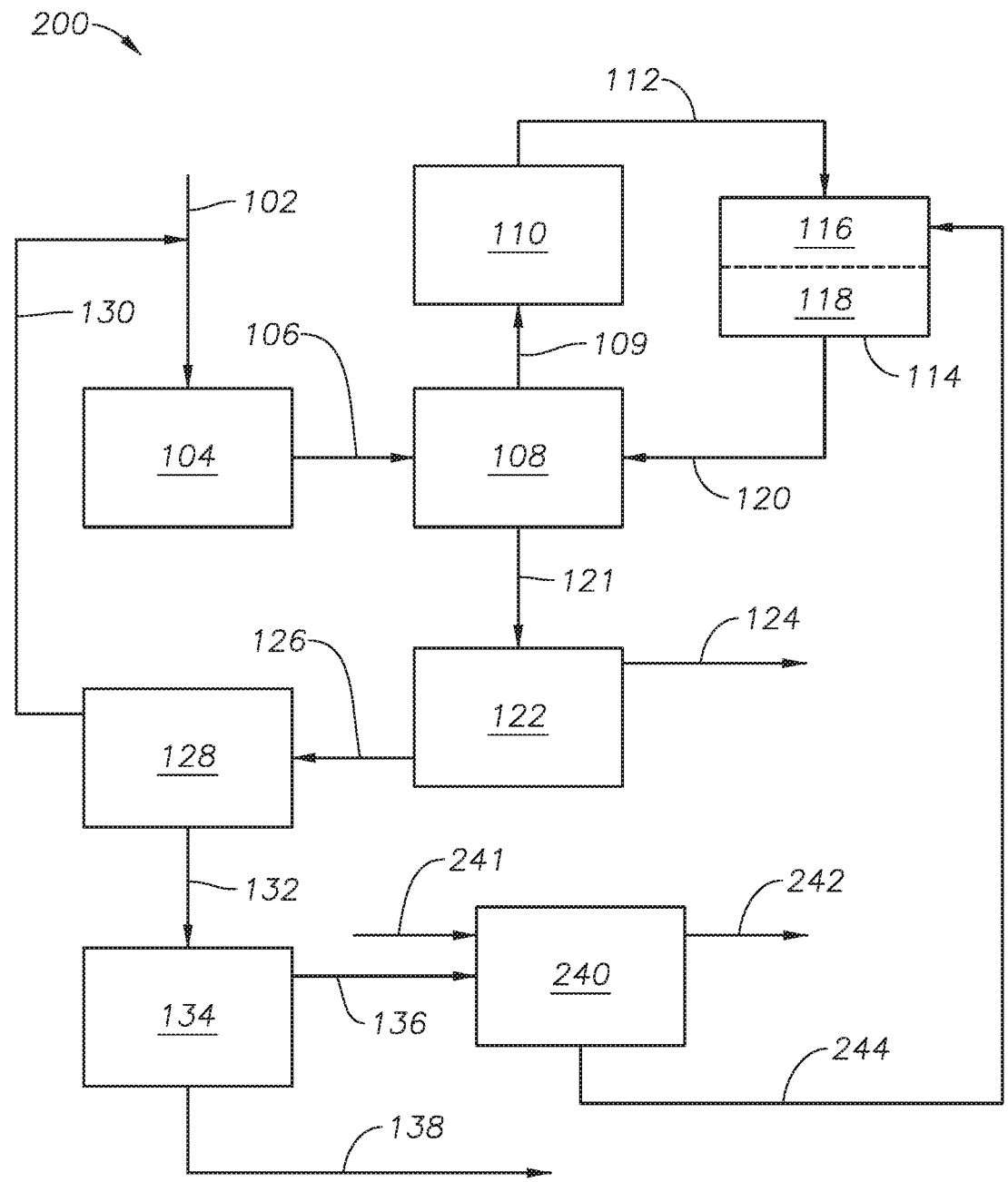
FIG. 2 is a block diagram of an ethylene production system with a dual-zone catalyst configuration and a MTBE unit, in accordance with another embodiment.

An advantage of the disclosed methods is the generation of the butene stream 136 that can be consumed in another process, such as an MTBE unit. FIG. 2 is a block diagram of an ethylene and MTBE production system 200 with a dual-zone catalyst configuration and an MTBE unit that can be understood with reference to FIG. 1. Referring to FIG. 2, this embodiment advantageously generates a butene residual 244 with an optimized and purified butene isomer composition that can be recycled to the reactor 114 to generate additional ethylene.

In certain embodiments, the butene stream 136 from the butene fractionation unit 134 is introduced into an extractive distillation column to produce a further enriched butene stream. In certain embodiments, isobutylene is separated from the other $C_4$ compounds in the butene stream 136.

In a preferred embodiment, the butene stream 136 from the butene fractionation unit 134 is supplied to an MTBE unit 240 along with a methanol stream 241. The MTBE unit 240 can be a standard MTBE unit known in the art, and can operate at temperature and pressure conditions standard for an MTBE unit known in the art. The MTBE unit 240 can be operated at about 40° C. to about 100° C., and about 100 psi to about 150 psi. The MTBE synthesis in the MTBE unit 240 can occur in a liquid phase via an exothermic reaction in the presence of an amount of acidic cation and exchange resin catalyst. The methanol stream 241 includes methanol. The MTBE unit 240 consumes the isobutylene from the butene stream 136. The MTBE unit 240 produces an MTBE product 242 and a butene residual 244. The MTBE product 242 can contain methyl tert-butyl ether (MTBE). The butene residual 244 can contain 1-butene, 2-butene, and isobutylene, and combinations of the same. The butene residual 244 can contain less than 10 wt % of isobutylene. The butene residual 244 can be recycled to the dual zone reactor 114 to further produce ethylene. In an embodiment, the butene residual 244 is supplied to a butene metathesis reactor.

EXAMPLES

The following examples are intended to be illustrative, and not limiting. As a result, it will be apparent for those skilled in the art that various modifications can be made from the illustrative embodiments and examples that are within the scope of the disclosure as defined by the appended claims.

Example 1

The process of FIG. 1 was simulated using Aspen Plus® (commercially available from Aspen Technology, Inc. headquartered in Bedford, Mass., USA) to determine overall product yields. An inlet stream of 10,000 kilograms per hour (kg/hr) of propylene was considered as feedstock in the integrated process. Reaction conditions include temperatures of 550° C. at 1 atm with a mesoporous silica catalysts impregnated with tungsten oxide ($WO_3/SiO_2$) as metathesis catalyst and MFI-2000 as cracking catalyst. About 4695 kg/hr of ethylene, 4562 kg/hr of mixed butenes, and about 731 kg/hr of $C_5+$ heavy products were produced.

Example 2

The process of FIG. 2 was simulated using Aspen Plus® (commercially available from Aspen Technology, Inc. headquartered in Bedford, Mass., USA) to determine overall product yields. An inlet stream of 10,000 kg/hr of propylene and about 1158 kg/hr of methanol were used as feedstock in the integrated process. Reaction conditions include temperatures of 550° C. at 1 atm. This resulted in product yields of about 4,695 kg/hr of ethylene, about 2,512 kg/hr of mixed butenes, and about 731 kg/hr of C5+ heavy products, in addition to about 33,208 kg/hr of MTBE.

Example 3

Experimental set-ups for the production of ethylene were evaluated using 0.5 g of 10 wt % $WO_3/SiO_2$ as the metathesis catalyst alone or in combination with two different catalysts positioned either upstream or downstream of the metathesis catalyst. Three experiments were performed. Reaction conditions for all three experiments include nitrogen being supplied at 25 ml/min and propylene being supplied at 5 ml/min.

Figure 3:
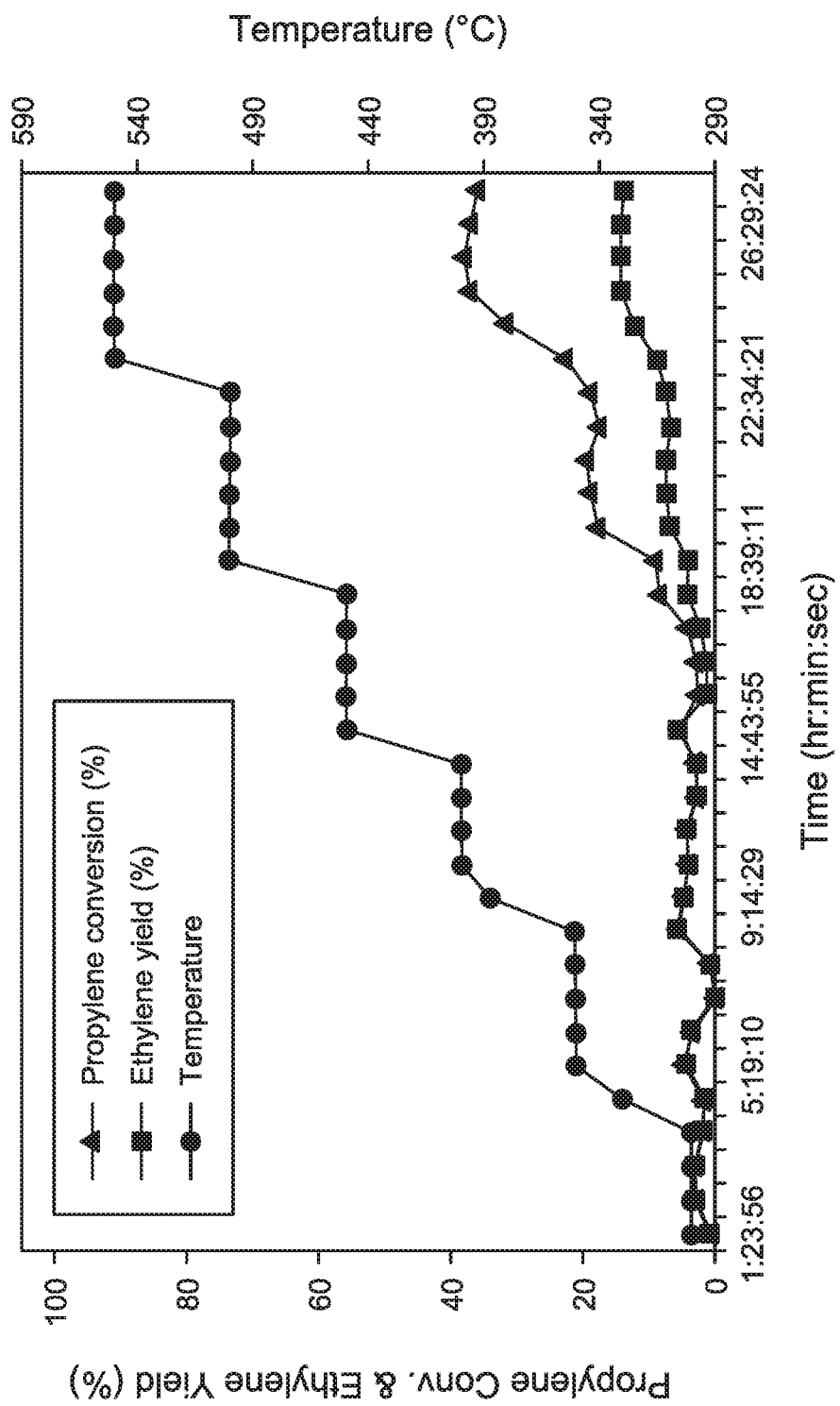
FIG. 3 is a graphical representation of the propylene conversion, ethylene yield, and temperature conditions for an ethylene production system, using a metathesis catalyst only.

Results of the first experiment from the metathesis catalyst alone are shown in FIG. 3. The hourly mass feed flow rate per mass of catalyst was 4.9 $h^{-1}$. FIG. 3 is a graphical representation of the propylene conversion, ethylene yield, and temperature conditions for an ethylene production system, using the metathesis catalyst only. Propylene was constantly converted to ethylene during the reaction time and resulted in about 38% conversion. As this reaction proceeds until equilibrium, ethylene yield increased to about 15%, with an ethylene selectivity of 38%. As the reaction is exothermic, the temperature of an ethylene production system increased from 295° C. to 545° C.

Figure 4:
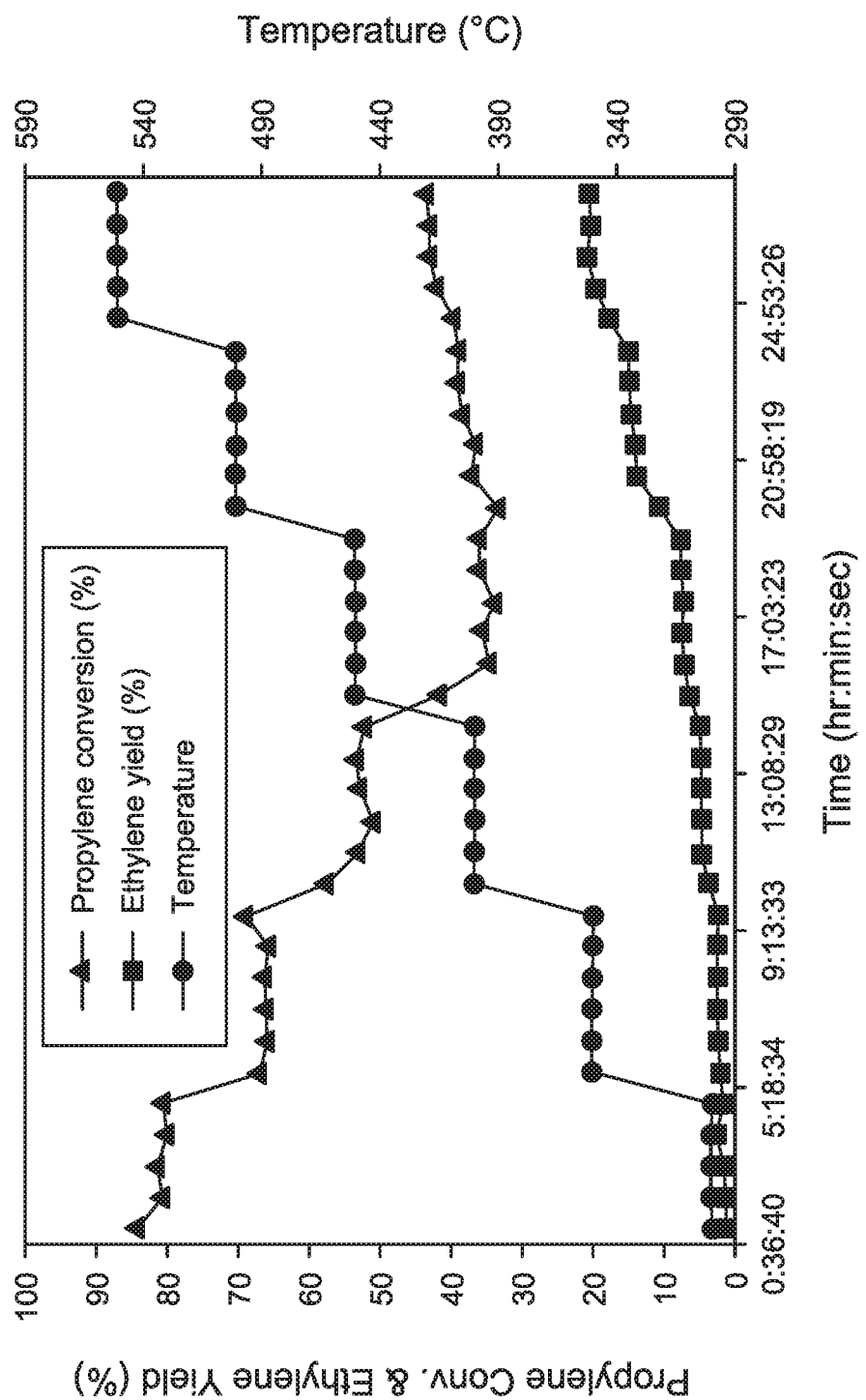
FIG. 4 is a graphical representation of the propylene conversion, ethylene yield, and temperature conditions for an ethylene production system using a metathesis catalyst positioned upstream of the cracking catalyst.

Results of the second experiment from the metathesis catalyst positioned upstream of a cracking catalyst are shown in FIG. 4. The experimental set-up for the production of ethylene includes a reactor with 0.5 g of 10 wt % $WO_3/SiO_2$ as the metathesis catalyst positioned upstream of 0.5 g of H-ZSM-5 (Si/Al=2000) as the cracking catalyst. Reaction conditions include nitrogen being supplied at 25 ml/min and propylene being supplied at 5 ml/min.

FIG. 4 is a graphical representation of the propylene conversion, ethylene yield, and temperature conditions for the third experiment of an ethylene production system using a metathesis catalyst positioned upstream of the H-ZSM-5 cracking catalyst. The propylene conversion curve in FIG. 4 starts at about 80%, as the metathesis of propylene is favored at lower temperatures in the dual catalyst system where the metathesis catalyst is positioned upstream of the cracking catalyst. In contrast, in FIGS. 3 and 5, when using the metathesis catalyst only or presenting the magnesium oxide isomerization catalyst upstream of the metathesis catalyst, no similar reaction happened at lower temperatures. The hourly mass feed flow rate per mass of catalyst was 2.4 $h^{-1}$. As shown in FIG. 4, propylene was constantly converted to ethylene during the reaction time. As this reaction proceeds until equilibrium, ethylene yield increased to about 20%, with an ethylene selectivity of 47%.

As the reaction is exothermic, the temperature of an ethylene production system increased from 295° C. to 545° C. The ethylene yield improved by 40% with the use of the metathesis catalyst upstream of the H-ZSM-5 cracking catalyst as compared to the use of the metathesis catalyst alone. The propylene conversion rate (single pass) was about 43 wt % with the use of the metathesis catalysts and H-ZSM-5 cracking catalysts as compared to 38% with the use of the metathesis catalyst alone. The selectivity of various products produced in this system is expressed as the percentage of the particular product produced (in moles) to the other products produced (in moles). Table 1 provides the selectivity of the various products produced in this system. The selectivity of various components based on the experiment data was calculated as follows. Using ethylene as an example, the selectivity profile is calculated as:

$$\text{Ethylene selectivity} \% = \frac{\text{ethylene produced in weight}}{\text{total converted Propylene in weight}}$$

TABLE 1

| Component | Selectivity % |
|---|---|
| Methane | 0.55% |
| Ethylene | 47.06% |
| Propane | 1.36% |
| 1-butene | 7.60% |
| Isobutylene | 21.18% |
| Cis-2-butene | 7.13% |
| Trans-2-butene | 9.27% |
| n-butane | 0.36% |
| iso-butane | 0.32% |
| C5/C5+ | 5.18% |

The yield of various products in this system is expressed as the percentage of the desired product produced (in moles) to the total amount that could have been made (if conversion of limiting reactant was 100% and no side reactions occurred). Table 2 provides the yield of the various products produced in this system. Using ethylene as an example and total propylene including both converted and unconverted propylene, the yield profile is calculated as:

$$\text{Ethylene yield} \% = \frac{\text{ethylene produced in weight}}{\text{total Propylene in weight}}$$

TABLE 2

| Component | Yield Percent |
|---|---|
| Methane | 0.24% |
| Ethane | 0.00% |
| Ethylene | 20.46% |
| Propane | 0.59% |
| Propylene | 56.52% |
| Isobutane | 0.16% |
| Butane | 0.14% |
| Trans-2-butene | 4.03% |
| 1-butene | 3.30% |
| Isobutylene | 9.21% |
| Cis-2-butene | 3.10% |
| Others | 2.25% |

Figure 5:
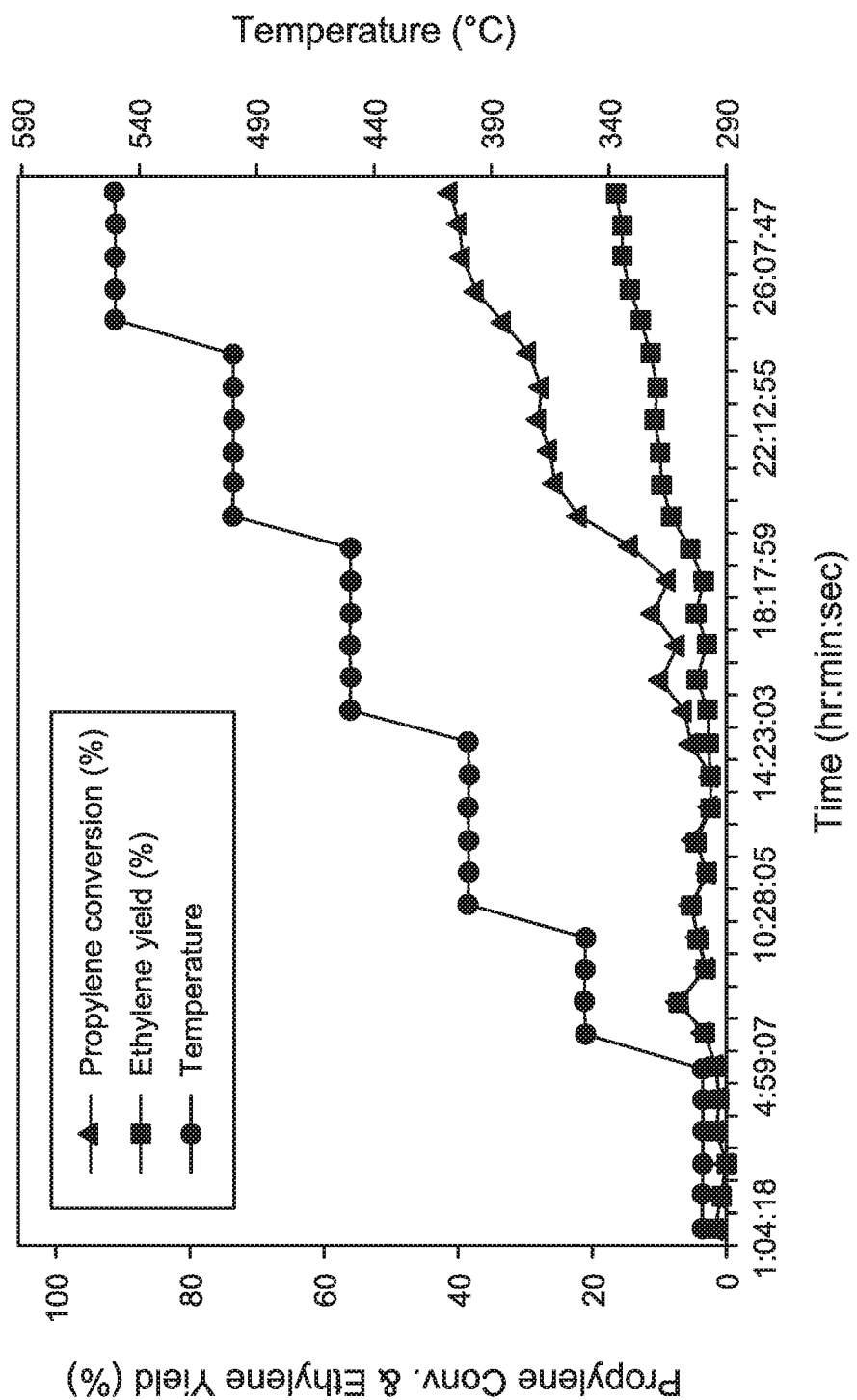
FIG. 5 is a graphical representation of the propylene conversion, ethylene yield, and temperature conditions for an ethylene production system using a metathesis catalyst positioned downstream of magnesium oxide functioning as an isomerization catalyst.

Results of an ethylene production system using a metathesis catalyst positioned downstream of magnesium oxide functioning as an isomerization catalyst are shown in FIG. 5. The experimental set-up for the production of ethylene includes a reactor with 0.5 g of 10 wt % $WO_3/SiO_2$ as the metathesis catalyst positioned upstream of 0.3 g of magnesium oxide (MgO). Reaction conditions include nitrogen being supplied at 25 ml/min and propylene being supplied at 5 ml/min.

FIG. 5 is a graphical representation of the propylene conversion, ethylene yield, and temperature conditions for an ethylene production system using a metathesis catalyst positioned downstream of the magnesium oxide catalyst. The hourly mass feed flow rate per mass of catalyst was 3.05 $h^{-1}$. As shown in FIG. 5, propylene was constantly converted to ethylene during the reaction time. As this reaction proceeds until equilibrium, ethylene yield increased to about 16%, with an ethylene selectivity of 39%. As the reaction is exothermic, the temperature of an ethylene production system increased from 295° C. to 545° C. The ethylene yield improved by 10% with the use of the metathesis catalyst downstream of the magnesium oxide catalyst as compared to the use of the metathesis catalyst alone. The propylene conversion rate (single pass) was about 41 wt % with the use of the metathesis and cracking catalysts as compared to 38% with the use of the metathesis catalyst alone.

Results from these three set-ups are summarized below in Table 3.

TABLE 3

| Catalyst | Hourly mass feed flow rate/catalyst mass ($h^{-1}$) | Propylene Conv. (%) | Selectivity (%) Ethylene | Yield (%) Ethylene | Wt % DELTA |
|---|---|---|---|---|---|
| Metathesis Catalyst | 4.875 | 38.17 | 38.31 | 14.62 | base |
| Metathesis Catalyst upstream of H-ZSM-5 Cracking Catalyst | 2.4375 | 43.48 | 47.06 | 20.46 | +39.9% |
| Metathesis Catalyst downstream of magnesium oxide catalyst | 3.047 | 41.05 | 39.20 | 16.09 | +10.0% |

It should be understood that any two quantitative values assigned to a property can constitute a range of that property, and all combinations of ranges formed from all stated quantitative values of a given property are contemplated in this disclosure. Having described the subject matter of the present disclosure in detail and by reference to specific embodiments, it is noted that the various details described in this disclosure should not be taken to imply that these details relate to elements that are essential components of the various embodiments described in this disclosure, even in cases where a particular element is illustrated in each of the drawings that accompany the present description. Further, it will be apparent that modifications and variations are possible without departing from the scope of the appended claims.

What is claimed is:

1. A method for producing ethylene and methyl tertiary-butyl ether (MTBE), the method comprising:

supplying a propylene feed stream comprising at least 80 weight percent propylene to a reactor, wherein the reactor comprises a metathesis reaction zone with a metathesis catalyst positioned upstream of a cracking reaction zone with a cracking catalyst;

at least partially metathesizing the propylene in the propylene feed stream with the metathesis catalyst to produce a metathesis reaction product, wherein the metathesis reaction product comprises butene and ethylene;

at least partially cracking the metathesis reaction product with the cracking catalyst to produce a cracking reaction product;

removing from the reactor a reactor product stream comprising propylene, butene, and ethylene;

fractionating the reactor product stream in an ethylene fractionation unit to produce an ethylene product and a C3+ stream comprising butene and propylene;

supplying the C3+ stream to a propylene fractionation unit;

fractionating the C3+ stream to produce a propylene recycle and a C4+ stream comprising butene;

supplying the C4+ stream to a butene fractionation unit;

fractionating the C4+ stream to produce a butene stream and a C5+ stream;

supplying the propylene recycle to the reactor; and supplying the butene stream to an MTBE unit.

2. The method of claim 1, further comprising the steps of:
supplying a methanol stream to the MTBE unit;
producing a butene residual in the MTBE unit, wherein the butene residual comprises 1-butene and 2-butene; and
producing an MTBE product in the MTBE unit, wherein the MTBE product comprises MTBE.

3. The method of claim 1, further comprising the step of removing impurities from a feed stream in an impurities removal unit to produce a clean propylene feed stream.

4. The method of claim 3, further comprising the step of heating the clean propylene feed stream in a heat exchanger to produce a hot propylene feed stream.

5. The method of claim 4, further comprising the step of heating the propylene feed stream using a heater to produce the propylene feed steam.

6. The method of claim 4, further comprising the step of cooling the reactor product stream in the heat exchanger, wherein the heat exchanger is a cross-exchanger.

7. The method of claim 1, wherein the propylene conversion rate in the reactor is greater than 40 percent.

8. The method of claim 2, wherein the butene residual further comprises isobutylene, wherein the isobutylene is present in an amount of less than about 10 weight percent of the butene residual.

9. The method of claim 1, wherein:
the metathesis catalyst comprises a mesoporous silica catalyst impregnated with metal oxide, wherein the mesoporous silica catalyst includes a pore size distribution of 2.5 nm to 40 nm and a total pore volume of at least 0.6 cm$^3$/g; and
the cracking catalyst comprises a mordenite framework inverted (MFI) structured silica catalyst with a total acidity ranging from 0.001 mmol/g to 0.1 mmol/g.

10. The method of claim 2, further comprising the step of recycling the butene residual to the reactor.

11. The method of claim 1, wherein the reactor is operated between about 500° C. and 600° C., and between about atmospheric pressure and 2 atmospheres of pressure.

12. A system for producing ethylene and methyl tertiary-butyl ether (MTBE), the system comprising:
a reactor, the reactor configured to convert a propylene feed stream to a reactor product stream, wherein the reactor comprises a metathesis reaction zone positioned upstream of a cracking reaction zone;
wherein the metathesis reaction zone comprises a metathesis catalyst comprising a mesoporous silica catalyst impregnated with metal oxide;
wherein the cracking reaction zone comprises a cracking catalyst comprising a mordenite framework inverted (MFI) structured silica catalyst;
wherein the reactor is configured to operate between about 500° C. and 600° C., and between about atmospheric pressure and 2 atmospheres of pressure, wherein the reactor product steam comprises propylene, ethylene, and butene;
an ethylene fractionation unit fluidically connected to the reactor, wherein the ethylene fractionation unit is configured to operate at a pressure and a temperature, to separate an ethylene product from the reactor product stream, wherein the ethylene fractionation unit further separates a C3+ stream;
a propylene fractionation unit fluidically connected to the ethylene fractionation unit, wherein the propylene fractionation unit is configured to operate at a pressure and a temperature, to separate a propylene recycle from the C3+ stream, wherein the propylene fractionation unit further separates a C4+ stream;
a butene fractionation unit fluidically connected to the propylene fractionation unit, wherein the butene fractionation unit is configured to operate at a pressure and a temperature to separate butene from the C4+ stream to produce a butene stream; and
an MTBE unit fluidically connected to the butene fractionation unit, wherein the MTBE unit is configured to produce a butene residual and an MTBE product from the butene stream.

13. The system of claim 12, wherein the metal oxide of the mesoporous silica catalyst comprises one or more oxides of molybdenum, rhenium, tungsten, or combinations thereof.

14. The system of claim 12, wherein the MFI structured silica catalyst is alumina free.

15. The system of claim 12, wherein the MFI structured silica catalyst comprises alumina.

16. The system of claim 12, wherein the MTBE unit is fluidically connected to the reactor, and further wherein the butene residual is supplied to the reactor.

17. The system of claim 12, further comprising an impurities removal unit fluidically connected upstream of the reactor.

18. The system of claim 12, further comprising a heater, the heater configured to heat the propylene feed stream before the propylene feed stream is introduced to the reactor.

19. The system of claim 12, further comprising a heat exchanger, the heat exchanger configured to heat the propylene feed stream before entering the reactor and cool the reactor product stream after leaving the reactor.

20. The system of claim 12, wherein the reactor is configured to react the propylene feed stream comprising greater than 80 weight percent of propylene to produce the reactor product stream comprising greater than 40 weight percent of ethylene.

* * * * *